United States Patent
Herrmann et al.

(10) Patent No.: US 6,762,282 B2
(45) Date of Patent: *Jul. 13, 2004

(54) HIGH YIELD S-NITROSYLATION PROCESS

(75) Inventors: Robert A. Herrmann, Boston, MA (US); David Knapp, Wellesley, MA (US)

(73) Assignee: SciMed Life Systems, Inc., Maple Grove, MN (US)

(*) Notice: Subject to any disclaimer, the term of this patent is extended or adjusted under 35 U.S.C. 154(b) by 0 days.

This patent is subject to a terminal disclaimer.

(21) Appl. No.: 10/436,965

(22) Filed: May 13, 2003

(65) Prior Publication Data

US 2003/0208036 A1 Nov. 6, 2003

Related U.S. Application Data

(63) Continuation of application No. 10/047,882, filed on Jan. 14, 2002, now abandoned, which is a continuation of application No. 09/645,171, filed on Aug. 24, 2000, now Pat. No. 6,417,347.

(51) Int. Cl.$^7$ .......................... C07K 1/113; C08B 37/16
(52) U.S. Cl. ...................... 530/336; 530/345; 530/402; 530/408; 530/409; 536/112; 536/124
(58) Field of Search ................................ 536/112, 124; 530/336, 345, 402, 408, 409; 568/76; 524/419

(56) References Cited

U.S. PATENT DOCUMENTS

| | | | |
|---|---|---|---|
| 5,025,001 A | 6/1991 | Loscalzo et al. | 514/91 |
| 5,380,758 A | 1/1995 | Stamler et al. | 514/562 |
| 5,385,937 A | 1/1995 | Stamler et al. | 514/557 |
| 5,574,068 A | 11/1996 | Stamler et al. | 514/562 |
| 5,583,101 A | 12/1996 | Stamler et al. | 514/2 |
| 5,593,876 A | 1/1997 | Stamler et al. | 435/188 |
| 5,612,314 A | 3/1997 | Stamler et al. | 514/13 |
| 5,648,393 A | 7/1997 | Stamler et al. | 514/562 |
| 5,703,073 A | 12/1997 | Garvey et al. | 514/226.5 |
| 5,770,645 A | 6/1998 | Stamler et al. | 524/419 |
| 5,863,890 A | 1/1999 | Stamler et al. | 514/561 |
| 6,057,367 A | 5/2000 | Stamler et al. | 514/561 |

OTHER PUBLICATIONS

Louis J. Ignarro et al., "Mechanism of Vascular Smooth Muscle Relaxation by Organic Nitrates, Nitrites, Nitroprusside and Nitric Oxide: Evidence for the involvement of S–Nitrosothiols as Active Intermediate," *Journal of Pharmacology and Experimental Therapeutics*, 1981, vol. 218(3), pp. 739–749.

Elizabeth A. Kowaluk et al., "Spontaneous Liberation of Nitric Oxide Cannot Account for in Vitro Vascular Relaxation by S–Nitrosothiols," *Journal of Pharmacology and Experimental Therapeutics*, 1990, vol. 255, pp. 1256–1264.

Joseph Loscalzo et al., "S–Nitrosocaptopril. I. Molecular Characterization and Effects of the Vascualture and on Platelets," *Journal of Pharmacology and Experimental Therapeutics*, 1989, vol. 249 (3), pp. 726–729.

Jonathan S. Stamler et al., "S–Nitrosylation of Proteins with Nitric Oxide: Synthesis and Characterization of Biologically Active Compounds," *Proceedings of the National Academy of Sciences*, Jan. 1992, vol. 89, pp. 444–448.

*Primary Examiner*—James O. Wilson
*Assistant Examiner*—Leigh C. Maier
(74) *Attorney, Agent, or Firm*—Mayer Fortkort & Williams, PC; David B. Bonham, Esq.

(57) ABSTRACT

A method for producing a S-nitrosylated species is provided. The method comprises: (a) providing a deoxygenated, alkaline aqueous solution comprising a thiol and a nitrite-bearing species; (b) acidifying the solution by adding acid to the solution while concurrently mixing the solution (e.g., by vigorously stirring the solution) to produce the S-nitrosylated species; and (c) isolating the S-nitrosylated species. The nitrite-bearing species can be, for example, an inorganic nitrite, such as an alkali metal nitrite, or an organic nitrite, such as an alkyl nitrite (e.g., ethyl nitrite, amyl nitrite, isobutyl nitrite or t-butyl nitrite). The thiol is preferably a thiol-containing polysaccharide, a thiol-containing lipoprotein, a thiol-containing amino acid or a thiol-containing protein, and more preferably a thiol-containing polysaccharide such as thiolated cyclodextrin. In many preferred embodiments, the S-nitrosylated species is insoluble in the acidified solution, precipitating upon formation. The S-nitrosylated species can be isolated, for example, by a process in which the precipitate is removed from the solution (e.g., by centrifugation) and the aqueous solvent remaining in the precipitate is sublimated (e.g., by freezing the precipitate and subjecting it to a vacuum). The isolated S-nitrosylated product is preferably protected from heat, light, moisture and oxygen.

20 Claims, No Drawings

HIGH YIELD S-NITROSYLATION PROCESS

This Application is a continuation of U.S. patent application Ser. No. 10/047,882, filed Jan. 14, 2002 now abandoned, entitled "High Yield S-Nitrosylation Process", which is a continuation of U.S. patent application Ser. No. 09/645,171, filed Aug. 24, 2000 entitled "High Yield S-Nitrosylation Process, now U.S. Pat. No. 6,417,347, issued Jul. 9, 2002.

FIELD OF THE INVENTION

The present invention relates to high-yield methods for producing S-nitrosylated compounds.

BACKGROUND OF THE INVENTION

S-nitrosylated compounds are compounds with one or more —S—NO groups. An —S—NO group is also referred to in the art as a sulfonyl nitrite, a thionitrous acid ester, an S-nitrosothiol or a thionitrite.

Various S-nitrosylated species are known and include:

a) Certain S-nitrosylated polysaccharides, such as S-nitrosylated starch, cellulose, alginic acid, K-carrageenan, fucoidin, and cyclodextrins (e.g., α-cyclodextrin, β-cyclodextrin and γ-cyclodextrin).
b) Certain lipoproteins substituted at the S-moiety with a nitric oxide moiety. Examples are chylomicron, a chylomicron remnant particle, a very low-density lipoprotein, a low-density lipoprotein, an intermediate-density lipoprotein, a high-density lipoprotein and a lipoprotein (a).
c) Certain S-nitrosylated polypeptides and proteins, such as neuropeptides, tissue-type plasminogen activator, streptokinase, urokinase, BSA, immunoglobulin (e.g., IgG, IgM, IgA, IgD, IgE), hemoglobin, myoglobin and cathepsin.
d) Certain S-nitroso amino acids and their derivatives (many of which are ACE inhibitors) including S-nitroso-N-acetylcysteine, S-nitroso-glutathione, S-nitroso-cysteine, S-nitroso-gamma-methyl-L-homocysteine, S-nitroso-L-homocysteine, S-nitroso-gamma-thio-L-leucine, S-nitroso-delta-thio-L-leucine, S-nitroso-captopril, N-acetyl-S-nitroso-D-cysteinyl-L-proline, N-acetyl-S-nitroso-D, L-cysteinyl-L-proline, 1-[5-guanidino-2-(S-nitroso) mercaptomethyl-pentanoyl]-L-proline, 1-[5-amino-2-(S-nitroso) mercaptomethyl-pentanoyl]-4-hydroxy-L-proline, 1-[5-guanidino-2-(S-nitroso)mercaptomethyl-pentanoyl]-4-hydroxy-L-proline, 1-[2-aminomethyl-3(S-nitroso)-mercaptomethyl-pentanoyl]-L-proline, and S-nitroso-L-cysteinyl-L-proline.
e) Certain other S-nitrosylated compounds such as S-nitroso-penicillamine, S-nitroso-N-acetylpenicillamine, and $Y(CH_2)_xSNO$, where x is 2–20 and Y can be —H, —SH, fluoro, $C_1$–$C_6$ alkoxy, cyano, carboxamido, $C_3$–$C_6$ cycloalkyl, aralkoxy, $C_2$–$C_6$ alkylsulfinyl, arylthio, $C_1$–$C_6$ alkylamino, $C_2$–$C_{15}$ dialkylamino, hydroxy, carbamoyl, $C_1$–$C_6$ N-alkylcarbamoyl, $C_2$–$C_{15}$ N,N-dialkylcarbamoyl, amino, hydroxyl, carboxyl, hydrogen, nitro or aryl; wherein aryl includes benzyl, naphthyl, and anthracenyl groups.

Several of these S-nitrosothiol species have been noted for their platelet inhibition and/or thrombolytic characteristics, as well as their ability to relax skeletal muscle and smooth muscle, including vascular smooth muscle (vasodilation), airway smooth muscle, gastrointestinal smooth muscle, corpus cavernosum smooth muscle, bladder smooth muscle, and uterine smooth muscle. For additional information, see, e.g., U.S. Pat. No. 5,770,645, U.S. Pat. No. 5,583,101, U.S. Pat. No. 5,863,890, U.S. Pat. No. 5,612,314, U.S. Pat. No. 5,648,393, U.S. Pat. No. 6,057,367 or U.S. Pat. No. 5,380,758, U.S. Pat. No. 5,593,876, U.S. Pat. No. 5,574,068 or U.S. Pat. No. 5,385,937, the disclosures of which are hereby incorporated by reference in their entireties.

U.S. Pat. No. 5,770,645, the entire disclosure of which is incorporated by reference immediately above, teaches that compounds with one or more free nucleophilic groups, such as polysaccharides that have been provided with pendant thiol groups, can be reacted with a nitrosylating agent under conditions suitable for nitrosylating the free thiol groups. Nitrosylating agents disclosed as suitable include acidic nitrite, nitrosyl chloride, compounds comprising an S-nitroso group (S-nitroso-N-acetyl-D, L-penicillamine (SNAP), S-nitrosoglutathione (SNOG), N-acetyl-S-nitrosopenicillaminyl-S-nitrosopenicillamine, S-nitrosocysteine, S-nitrosothioglycerol, S-nitrosodithiothreitol and S-nitrosomercaptoethanol), an organic nitrite (e.g. ethyl nitrite, isobutyl nitrite, and amyl nitrite), peroxynitrites, nitrosonium salts (e.g. nitrosyl hydrogen sulfate), oxadiazoles (e.g. 4-phenyl-3-furoxancarbonitrile) and the like. For more information, see U.S. Pat. No. 5,770,645.

SUMMARY OF THE INVENTION

According to an embodiment of the invention, a method for producing a S-nitrosylated species is provided. The method comprises: (a) providing a deoxygenated, alkaline aqueous solution comprising a thiol and a nitrite-bearing species; (b) acidifying the solution by adding acid to the solution while concurrently mixing the solution (e.g., by vigorously stirring the solution) to produce the S-nitrosylated species; and (c) isolating the S-nitrosylated species.

The aqueous solution can be rendered alkaline, for example, by adding an alkali metal hydroxide.

The solution can be deoxygenated, for example, by drawing a vacuum, by purging with an inert gas (such as nitrogen), or by first drawing a vacuum followed by purging with an inert gas.

The nitrite-bearing species can be, for example, an inorganic nitrite, such as an alkali metal nitrite, or an organic nitrite, such as an alkyl nitrite (e.g., ethyl nitrite, amyl nitrite, isobutyl nitrite or t-butyl nitrite).

The thiol is preferably a thiol-containing polysaccharide, a thiol-containing lipoprotein, a thiol-containing amino acid or a thiol-containing protein, and more preferably a thiol-containing polysaccharide such as thiolated cyclodextrin.

Preferably, 1 to 2 equivalents of nitrite-bearing species are provided per thiol equivalent.

The acid can be, for example, an inorganic acid, such as hydrochloric acid, phosphoric acid or sulfuric acid, or an organic acid, such as acetic acid. Preferably, the acid is added to the solution in an amount effective to provide at least 70% of theoretical yield within at least 1 hour.

The S-nitrosylated species is preferably insoluble in the acidified solution, precipitating upon formation. The S-nitrosylated species can be isolated, for example, by a process in which the precipitate is removed from the solution (e.g., by centrifugation) and the aqueous solvent remaining in the precipitate is sublimated (e.g., by freezing the precipitate and subjecting it to a vacuum).

The isolated S-nitrosylated product is preferably protected from heat, light, moisture and oxygen.

In one particularly preferred embodiment of the invention, a method for producing an S-nitrosylated cyclodextrin species is provided. The method comprises: (a) providing a deoxygenated, alkaline aqueous solution comprising a thiolated cyclodextrin and a nitrite-bearing species selected from an alkali metal nitrite and an alkyl nitrite; (b) acidifying the solution by adding acid to the solution, while concurrently mixing the solution, to produce an S-nitrosylated cyclodextrin species precipitate; and (c) removing the precipitate from the solution. 1 to 2 equivalents of nitrite-bearing species are preferably provided per thiol equivalent. Moreover, the method preferably comprises sublimating any aqueous solvent remaining in the precipitate after removal from the solution (e.g., by freezing the precipitate and subjecting it to a vacuum). It is also preferable to protect the sublimated S-nitrosylated cyclodextrin species precipitate from heat, light, moisture and oxygen.

One advantage of the present invention is that S-nitrosylated species are produced under conditions that minimize exposure to environmental conditions that result in premature breakdown and NO release.

Another advantage of the present invention is that thiol species can be nitrosylated in high yield.

Yet another advantage of the present invention is that a S-nitrosylated species can be produced in the form of a fine powder, eliminating the need for crushing or otherwise milling the product.

These and other embodiments and advantages of the present invention will become readily apparent to those of ordinary skill in the art upon review of the Detailed Description and claims to follow.

DETAILED DESCRIPTION OF THE INVENTION

According to one aspect of the invention, S-nitrosylated species are produced by first providing a deoxygenated, alkaline aqueous solution comprising a thiol and a nitrite-bearing species, and subsequently acidifying this solution by adding acid with concurrent vigorous mixing.

Essentially any nitrite-bearing species that is soluble in basic solution and is capable of nitrosylating free thiol groups under acidic conditions can be used. Preferred nitrite-bearing species include organic nitrites and inorganic nitrites. Preferred organic nitrites are alkyl nitrites, more preferably $C_1$–$C_8$ linear or branched alkyl nitrites, such as ethyl nitrite, amyl nitrite, isobutyl nitrite and t-butyl nitrite. Preferred inorganic nitrites are alkali metal nitrites such as sodium nitrite, lithium nitrite, and potassium nitrite.

A wide range of base-soluble thiol species can be S-nitrosylated in accordance with the present invention, so long as any undesirable side reactions are kept to a minimum. Several S-nitrosylated products of thiol species are discussed in the Background section above. Preferred thiol species include thiol-containing polysaccharides, thiol-containing lipoproteins, thiol-containing amino acids and thiol-containing proteins.

In some embodiments of the present invention, it is desirable to provide a species with thiol groups for subsequent S-nitrosylation. For example, a thiolated species can be formed from a species having one or more pendant nucleophilic groups, such as alcohols or amines. These pendant nucleophilic groups can be converted to pendant thiol groups by methods known in the art, such as those disclosed in Gaddell and Defaye, Angew. Chem. Int. Ed. Engl. 30:78 (1991) and Rojas et al., J. Am. Chem. Soc. 117:336 (1995), the teachings of which are hereby incorporated into this application by reference.

As a specific example, polysaccharides typically do not have thiol groups, but do have pendant alcohol groups. For instance, particularly preferred polysaccharides for the practice of the invention include cyclodextrins such as:

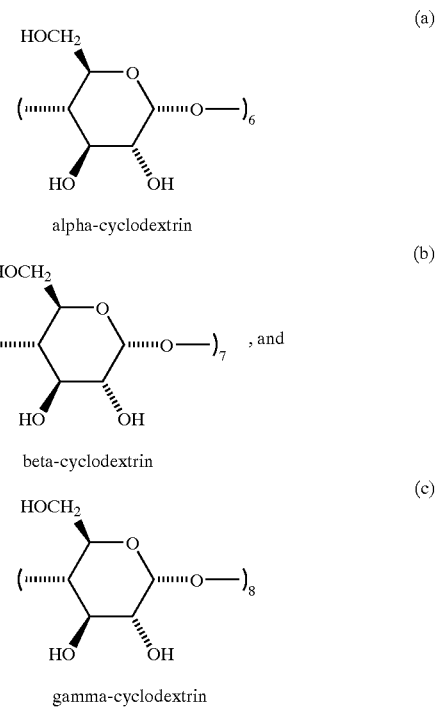

In accordance with the present invention, prior to S-nitrosylation, the polysaccharide is first converted to a polythiolated polysaccharide using, for example, the methods disclosed above. In these methods, primary alcohols are thiolated preferentially over secondary alcohols. In some preferred embodiments, a sufficient excess of thiolating reagent is used to form perthiolated polysaccharides. Polysaccharides are "perthiolated" when all of primary alcohols have been converted to thiol groups. As seen from the above, alpha-cyclodextrin has six primary alcohols, beta-cyclodextrin has seven primary alcohols and gamma-cyclodextrin has eight primary alcohols. Hence, perthiolated alpha-cyclodextrin has six thiol groups, perthiolated beta-cyclodextrin has seven thiol groups and perthiolated gamma-cyclodextrin has eight thiol groups.

Further details and a specific procedure in which beta-cyclodextrin can be converted to per-(6-deoxy-6-thio)-beta-cyclodextrin are found in U.S. Pat. No. 5,770,645 (see, inter alia, Examples 1 and 2).

U.S. Pat. No. 5,770,645 also teaches that a polythiolated species can be prepared by reacting a polyhydroxylated species, and preferably the primary alcohol groups of the polyhydroxylated species, with a reagent that adds a moiety containing a free thiol or protected thiol to the alcohol. In one example the polysaccharide is reacted with a bis isocyanatoalkyldisulfide followed by reduction to functionalize the alcohol as shown in Structural Formula (I):

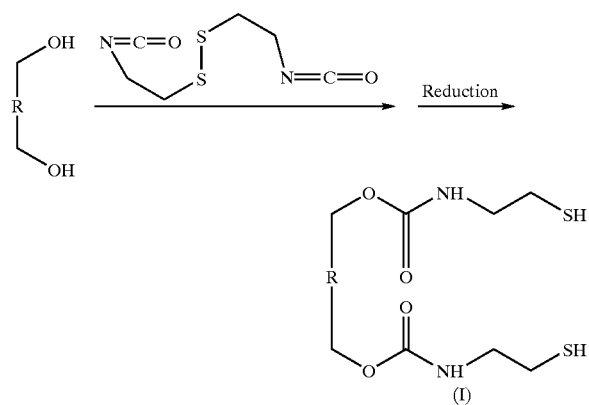

Conditions for carrying out this reaction are found in Cellulose and its Derivatives, Fukamota, Yamada and Tonami, Eds. (John Wiley & Sons), Chapter 40, (1985) the teachings of which are incorporated herein by reference. One example of a polythiolated polysaccharide that can be obtained by this route is shown in Structural Formula (II):

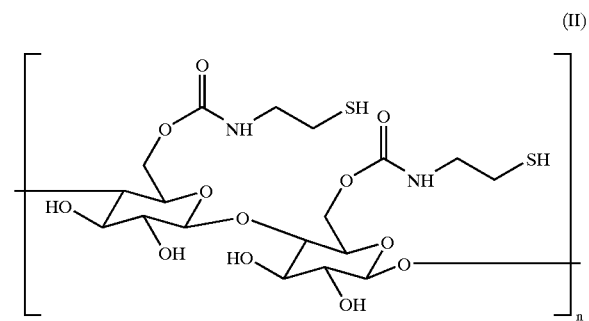

Once obtained, the desired thiol and nitrite-bearing species are combined in an alkaline aqueous solution.

Preferably, the solution is provided with 1 to 2 equivalents of nitrite for each thiol equivalent. The thiol bearing species is not necessarily fully nitrosylated using this range of nitrite. For example, in the case of perthiolated beta-cyclodextrin, which contains seven thiol groups per molecule, this range typically provides on the order of about one S-nitroso group per cyclodextrin molecule.

In general, the solution should be sufficiently alkaline to prevent premature and significant nitrosylation of the thiol groups and to prevent precipitation of material under non-ideal conditions. Essentially any basic material can be used to render the solution alkaline. Alkali metal hydroxides are preferred, most preferably lithium, potassium or sodium hydroxide.

While the solution should be sufficiently alkaline to prevent significant nitrosylation of the thiol groups, additional base can be added beyond this point, if necessary to assist in dissolving the thiol species. The appropriate pH to achieve each of these objectives will vary depending, for example, on the thiol species and nitrite-bearing species selected, but it can be readily be determined by those of ordinary skill in the art.

The order of addition of thiol, nitrite-bearing species and base is unimportant, so long as the solution is sufficiently alkaline at the point where the thiol becomes associated with the nitrite-bearing species in solution. For example, (1) the thiol can first be dissolved in the basic solution, followed by the nitrite-bearing species, (2) the nitrite-bearing species can first be dissolved in the basic solution, followed by the thiol species, (3) the nitrite-bearing species and the thiol can be dissolved in the basic solution at the same time, and so forth.

As a specific example, a 0.1 NaOH solution (having a pH of about 13) can be used as a starting solution, with thiol and the nitrite-bearing species added in turn.

Degradation of nitrosylated thiols (i.e., the release of NO and reversion to the thiol form) is accelerated upon exposure to oxygen, moisture, heat and/or light. Hence, in accordance with the present invention, it is desirable to reduce exposure to these conditions during production and storage to the greatest extent possible.

In this connection and in accordance with the present invention, the solution is deoxygenated prior to the formation of the S-nitrosylated species (i.e., prior to acidification of the alkaline solution containing the thiol species and the nitrite-bearing species). As specific examples, prior to acidification, (1) the basic solution can first be deoxygenated, followed by dissolution of the thiol species and nitrite-bearing species in the same (2) the thiol species and nitrite-bearing species can first be dissolved in the basic solution, followed by deoxygenation, (3) the thiol species can first be dissolved in the basic solution, followed by deoxygenation and dissolution of the nitrite-bearing species, (4) the nitrite-bearing species can be dissolved in the basic solution, followed by deoxygenation and dissolution of the thiol species, and so forth.

A given solution can be deoxygenated by using any of several known methods. For example, the solution can be placed in a closed container followed by (1) drawing a vacuum, (2) purging the overhead space with an inert gas, (3) bubbling the solution with an inert gas, (4) heating to near boiling, and so forth. In one preferred technique, the solution is deoxygenated by first drawing a vacuum. Then, the vacuum is eliminated by purging the overhead space with an inert gas. Preferred inert gases for the above applications include nitrogen and argon.

Once a deoxygenated, basic aqueous solution of the thiol species and the nitrite-bearing species is obtained, the solution is subsequently acidified, preferably accompanied by vigorous mixing.

The acid is preferably added to the solution in an amount effective to provide at least 70% of the theoretical yield within 24 hours, more preferably within 1 hour, most preferably 10 minutes. The precise pH required to achieve this outcome will vary, depending on the thiol species and nitrite-bearing species selected, and it can be readily determined by those of ordinary skill in the art.

Essentially any acid can be used for this purpose so long as undesirable side reactions are kept to a minimum. Preferred acids for the practice of the present invention include both inorganic acids, such as hydrochloric acid, phosphoric acid and sulfuric acid, and organic acids, such as acetic acid.

Vigorous mixing is carried out to minimize concentration gradients in the solution while the nitrosylation reaction takes place. Mixing can be realized by known methods that include contacting the fluid with a moving member such as a stir bar or paddle, directing the fluid into a stationary member such as a baffle, and so forth.

Various benefits can be garnered by mixing the solution, particularly where the reaction proceeds very quickly.

For instance, where multiple reaction sites are available, product uniformity is enhanced. As a specific example, perthiolated beta-cyclodextrin has seven available thiol sites for reaction. Based on the reaction stoichiometry, however, only about one of these sites is nitrosylated on average. While not wishing to be bound by theory, it is believed that since this reaction proceeds rapidly, if concentration gradients are allowed to persist in the solution after the acid is added even for a short period of time, the beta-cyclodextrin molecules in the more acidic environments will have more nitrosylated sites (due to more favorable reaction kinetics) than those in less acidic environments.

As another example, where the resulting S-nitrosylated species is insoluble in the acidified solution and precipitates from solution upon formation, a finer precipitate product is typically obtained by vigorously mixing during acid addition than would otherwise be obtained in the absence of such mixing.

Each of the above procedures of the present invention is preferably conducted at a temperature within the range of from about 0° C. to about 50° C., more preferably at room temperature.

After the S-nitrosylated species is formed, it is preferably isolated and dried to provide the product in powder form. In preferred embodiments of the invention, the S-nitrosylated species precipitates from solution upon formation.

In particularly preferred embodiments of the present invention, this precipitate is first isolated in wet form from the aqueous solvent (e.g., by centrifugation), washed in deionized water and remaining solvent in the wet sample removed by sublimation (e.g., lyophilization or freeze drying). The sublimation process acts to protect the sample from degradation (e.g., because moisture and oxygen are removed), and it promotes the formation of a very fine powder. As a specific example, where the precipitate is S-nitrosylated cyclodextrin, and where the sample is allowed to dry in air, substantial clumps form. In contrast, where the precipitate is dried by sublimation, a fine powder is produced, and conditions are maintained which are less prone to degrade the final product.

Preferably, the wet precipitate is sublimated by first freezing it (e.g., by cooling the sample to −70° C. or by immersion in liquid nitrogen). The frozen precipitate is then placed in a container, and a vacuum is drawn, whereupon the aqueous solvent is sublimated from the frozen precipitate.

Once a dry product is formed, steps are preferably taken to avert premature product degradation. For example, the product is preferably kept in a cool and dark place, such as a refrigerator or freezer. For additional protection, the environment surrounding the sample is preferably an inert, water-free environment, and is more preferably a vacuum environment or a desiccated, inert gas environment.

EXAMPLE 4 grams of beta-cyclodextrin thiol are initially provided. (Beta-cyclodextrin thiol can be prepared for example, using the procedures of Examples 1 and 2 of U.S. Pat. No. 5,770,645, the entire disclosure of which is incorporated by reference.) Then, a 300 ml portion of 0.1 N NaOH (which has a pH of approximately 13.0) is added to the beta-cyclodextrin thiol. After mixing to dissolve the cyclodextrin thiol, the solution is filtered through a 0.45 micron filter. 1.6 grams of sodium nitrite ($NaNO_2$) are then added. After mixing to dissolve the sodium nitrite, the solution is divided into 25 ml aliquots. For each aliquot, the following procedure is performed:

1. The solution is degassed by applying a vacuum, after which the removed gas is either replaced with nitrogen or the solution is kept under vacuum.
2. Under nitrogen or vacuum, 300 ml of 0.1 N HCl are quickly injected into the solution accompanied by vigorous stirring.
3. The mixture is reacted for 5 minutes, over which time a pink precipitate is formed.
4. The mixture is then centrifuged at 4000 rpm (approx. 800×g) for 10 minutes.
5. The supernatant is removed.
6. The precipitate is washed by suspending it in degassed de-ionized water, followed by centrifugation and recovery of the precipitate.
7. After repeating the prior washing step three times, the recovered precipitate is immediately frozen in liquid nitrogen for 5 minutes.
8. The frozen material is then lyophilized (sublimated under vacuum) until dry (typically over a period of several days).
9. Once dry, the material is stored under nitrogen at −20° C.

Although various embodiments are specifically illustrated and described herein, it will be appreciated that modifications and variations of the present invention are covered by the above teachings and are within the purview of the appended claims without departing from the spirit and intended scope of the invention.

What is claimed is:

1. A method for producing an S-nitrosylated species comprising:
   providing a deoxygenated, alkaline aqueous solution comprising a thiol and a nitrite-bearing species;
   combining said solution with an acid with concurrent mixing to produce said S-nitrosylated species; and
   isolating and drying said S-nitrosylated species to form a powder.

2. The method of claim 1, wherein said aqueous solution is rendered alkaline by combining said thiol with a basic material.

3. The method of claim 2, wherein said basic material is an alkali metal hydroxide.

4. The method of claim 1, wherein said solution is deoxygenated by drawing a vacuum.

5. The method of claim 1, wherein said solution is deoxygenated by purging with an inert gas.

6. The method of claim 5, wherein said inert gas comprises nitrogen or argon.

7. The method of claim 1, wherein 1 to 2 equivalents of nitrite-bearing species are provided per thiol equivalent.

8. The method of claim 1, wherein said nitrite-bearing species is an inorganic nitrite.

9. The method of claim 8, wherein said inorganic nitrite is an alkali metal nitrite.

10. The method of claim 1, wherein said nitrite-bearing species is an organic nitrite.

11. The method of claim 10, wherein said organic nitrite is an alkyl nitrite.

12. The method of claim 1, wherein said acid is an inorganic acid.

13. The method of claim 1, wherein said acid is an organic acid.

14. The method of claim 1, wherein said thiol is selected from a thiol-containing polysaccharide, a thiol-containing lipoprotein, a thiol-containing amino acid and a thiol-containing protein.

15. The method of claim 14, wherein said thiol-containing polysaccharide is thiolated cyclodextrin.

16. The method of claim 1, wherein amid S-nitrosylated species is insoluble in said acidified solution and forms a precipitate.

17. The method of claim 16, wherein the S-nitrosylated species is isolated and dried by a process comprising centrifuging and drying said S-nitrosylated species to form said powder.

18. The method of claim 16, wherein the S-nitrosylated species is isolated and dried by a process comprising:
removing said precipitate from solution and
sublimating aqueous solvent remaining in said precipitate.

19. The method of claim 18, wherein said sublimating step comprises freezing said precipitate and subjecting said precipitate to a vacuum.

20. The method of claim 1, wherein said S-nitrosylated species is isolated and dried by a process comprising a sublimating step.

* * * * *

UNITED STATES PATENT AND TRADEMARK OFFICE
CERTIFICATE OF CORRECTION

PATENT NO.   : 6,762,282 B2
DATED        : July 13, 2004
INVENTOR(S)  : Robert A. Herrmann et al.

It is certified that error appears in the above-identified patent and that said Letters Patent is hereby corrected as shown below:

Column 10,
Line 5, after "wherein", change "amid" to -- said --.

Signed and Sealed this

Fourteenth Day of December, 2004

JON W. DUDAS
*Director of the United States Patent and Trademark Office*

UNITED STATES PATENT AND TRADEMARK OFFICE
CERTIFICATE OF CORRECTION

PATENT NO.   : 6,762,282 B2
DATED        : July 13, 2004
INVENTOR(S)  : Robert A. Herrmann et al.

It is certified that error appears in the above-identified patent and that said Letters Patent is hereby corrected as shown below:

Column 10,
Line 5, after "wherein", change "amid" to -- said --.

Signed and Sealed this

Twenty-first Day of December, 2004

JON W. DUDAS
*Director of the United States Patent and Trademark Office*